United States Patent
Schepis et al.

(10) Patent No.: US 10,485,971 B2
(45) Date of Patent: Nov. 26, 2019

(54) NON-INVASIVE NERVE STIMULATION SYSTEM AND METHOD

(71) Applicant: Avent, Inc., Alpharetta, GA (US)

(72) Inventors: Eric A. Schepis, Alpharetta, GA (US); Carolyn Y. Sargent, Atlanta, GA (US)

(73) Assignee: Avent, Inc., Alpharetta, GA (US)

(*) Notice: Subject to any disclaimer, the term of this patent is extended or adjusted under 35 U.S.C. 154(b) by 163 days.

(21) Appl. No.: 15/522,826

(22) PCT Filed: Oct. 28, 2015

(86) PCT No.: PCT/US2015/057710
§ 371 (c)(1),
(2) Date: Apr. 28, 2017

(87) PCT Pub. No.: WO2016/069689
PCT Pub. Date: May 6, 2016

(65) Prior Publication Data
US 2017/0333706 A1    Nov. 23, 2017

Related U.S. Application Data

(60) Provisional application No. 62/073,302, filed on Oct. 31, 2014.

(51) Int. Cl.
*A61N 1/36* (2006.01)
*A61N 1/04* (2006.01)

(52) U.S. Cl.
CPC ......... *A61N 1/3601* (2013.01); *A61N 1/0456* (2013.01); *A61N 1/0472* (2013.01); *A61N 1/0476* (2013.01); *A61N 1/36031* (2017.08); *A61N 1/048* (2013.01); *A61N 1/36021* (2013.01)

(58) Field of Classification Search
CPC ............... A61N 1/3601; A61N 1/0472; A61N 1/36031; A61N 1/0476; A61N 1/0456; A61N 1/048; A61N 1/36021
See application file for complete search history.

(56) References Cited

U.S. PATENT DOCUMENTS

| | | |
|---|---|---|
| 2,535,788 A | 12/1950 | Sarnoff |
| 2,664,880 A | 1/1954 | Wales, Jr. |
| 4,827,935 A | 5/1989 | Geddes et al. |
| 5,056,519 A | 10/1991 | Vince |
| 5,449,378 A | 9/1995 | Schouenborg |
| 6,360,740 B1 | 3/2002 | Ward et al. |
| 6,463,327 B1 | 10/2002 | Lurie et al. |

(Continued)

FOREIGN PATENT DOCUMENTS

| | | |
|---|---|---|
| EP | 1 393 773 B1 | 10/2006 |
| EP | 2 174 589 A1 | 4/2010 |

(Continued)

OTHER PUBLICATIONS

International Search Report for PCT/US2015/057710, dated Dec. 22, 2014, 4 pages.

*Primary Examiner* — Christopher Koharski
*Assistant Examiner* — Natasha Patel
(74) *Attorney, Agent, or Firm* — Dority & Manning, P.A.

(57) ABSTRACT

A system and method for the transcutaneous stimulation of various nerves such as the phrenic, hypoglossal, and vagal nerves is provided. The stimulation elicits a corresponding muscle response without reported pain.

20 Claims, 14 Drawing Sheets

(56) References Cited

U.S. PATENT DOCUMENTS

| | | | |
|---|---|---|---|
| 6,587,726 B2 | 7/2003 | Lurie et al. | |
| 7,277,757 B2 | 10/2007 | Casavant et al. | |
| 7,840,270 B2 | 11/2010 | Ignagni et al. | |
| 7,979,128 B2 | 7/2011 | Tehrani et al. | |
| 2005/0085869 A1 | 4/2005 | Tehrani et al. | |
| 2006/0052834 A1 | 3/2006 | Goroszeniuk | |
| 2006/0224209 A1 | 10/2006 | Meyer | |
| 2006/0258667 A1 | 11/2006 | Teng | |
| 2008/0147146 A1 | 6/2008 | Wahlgren et al. | |
| 2009/0312688 A1 | 12/2009 | Reddy et al. | |
| 2010/0016929 A1* | 1/2010 | Prochazka | A61B 5/0028 607/72 |
| 2010/0152808 A1* | 6/2010 | Boggs, II | A61N 1/0456 607/46 |
| 2010/0198298 A1* | 8/2010 | Glukhovsky | A61N 1/36021 607/46 |
| 2010/0274329 A1 | 10/2010 | Bradley et al. | |
| 2011/0190845 A1 | 8/2011 | Weisfeldt et al. | |
| 2013/0085551 A1* | 4/2013 | Bachinski | A61N 1/36014 607/59 |
| 2013/0158627 A1 | 6/2013 | Gozani et al. | |
| 2013/0238066 A1* | 9/2013 | Boggs, II | A61N 1/0558 607/116 |
| 2014/0148872 A1 | 5/2014 | Goldwasser et al. | |
| 2015/0257970 A1* | 9/2015 | Mucke | A61N 1/0476 601/21 |

FOREIGN PATENT DOCUMENTS

| | | |
|---|---|---|
| JP | 2007151747 A | 6/2007 |
| WO | WO 2011/044176 A1 | 4/2011 |

\* cited by examiner

NON-INVASIVE NERVE STIMULATION SYSTEM AND METHOD

RELATED APPLICATION

The present application is the national stage entry of International Patent Application No. PCT/US2015/057710 having a filing date of Oct. 28 2015, which claims priority to U.S. provisional application Ser. No. 62/073,302, filed on Oct. 31, 2014, both of which are incorporated herein in their entirety by reference thereto.

FIELD OF THE INVENTION

The disclosure generally relates to a medical device and method for non-invasively stimulating nerves to cause targeted muscle contractions.

BACKGROUND OF THE DISCLOSURE

In one instance, a person may need respiratory assistance as a result of disease and injuries of various kinds. The respiratory assistance can encompass everything from facilitating spontaneous breathing to full-time respiratory pacing. Typically, a mechanical ventilator is employed to provide the needed level of respiratory assistance.

Studies show that long-term respiratory support leads to diaphragm muscle weakness. The diaphragm muscle is largely responsible for a person's ability to inspire and will begin to atrophy as soon as 18 hours following continuous ventilator support. The severity of atrophy is exacerbated over time. In many instances, the atrophy is so severe that the person loses the ability to breathe spontaneously upon removal of the respirator.

When persons cannot breathe reliably on their own, they must undergo a weaning process designed to free them from the respirator. The weaning process may last days, weeks or months, and is dependent on the severity of the atrophy. Weaning over a long term increases a person's discomfort level and risk of developing a secondary disease (e.g., pneumonia).

The time-course and various challenges of weaning are important to the caregiver and health care provider. Between 1.2 and 1.8 million persons fail at least 1 weaning attempt per year. Long-term weaning can contribute to a loss of life. Furthermore, about 6 million people are mechanically ventilated each year at a cost of approximately $1,500.00 per patient per day. The weaning period accounts for about 42% of the time people are mechanically ventilated. This adds to the overall cost of medical care.

Diaphragm atrophy is a recognized issue in persons with spinal cord injuries, and it is reversible. Electrical stimulation of the phrenic nerves via implanted electrodes is used to strengthen the weakened diaphragm muscle in spinal cord injured persons who are preparing for full-time respiratory pacing. The conditioning period is variable, ranging from 3 to 16 months, and is dependent on the severity of the atrophy.

The invasive method of causing the diaphragm muscle to contract carries with it a risk of infection, a need for surgery and inpatient stays, discomfort due to having electrodes implanted into the body, and higher costs for the person to bear. Thus, non-invasive methods of causing contraction of the diaphragm muscle are preferred for any patient undergoing a weaning or conditioning process. Building on the success of using implanted devices to condition atrophied diaphragm muscles, non-invasive electric methods have been explored.

It has been shown that transcutaneous, electrical-stimulation of the human neck region can activate the phrenic nerves and drive contraction of the diaphragm muscle. Studies have elicited diaphragm muscle contraction with surface electrical stimulation to investigate breathing muscle atrophy. Specifically, the application of a single pulse of electrical stimulation (e.g., >1 ms pulse duration) to the neck region where the phrenic nerve is located can elicit maximal diaphragmatic pressures in humans. Shorter pulse durations (100 µs) of monophasic or biphasic constant-voltage square-wave pulses with large stimulation amplitudes (approaching 300 V) can also be used to achieve maximal diaphragm muscle contraction.

Despite these accomplishments, several problems prevent these methods from being successful. One problem is the activation of pain receptors in the proximity of the electrodes (i.e., neck). This pain sensation is reported to be quite significant, and is caused by activation of nociceptors that are located in the skin beneath the electrodes. Painful treatment methods can cause a patient to undergo extreme stress in anticipation of and during treatment. Another problem is the difficulty in placing the electrode at the appropriate area of the neck. If initially the electrode is not placed correctly, the diaphragm will not contract and unwanted muscle contractions from superficial musculature will result. This will require a painful search for the ideal stimulation site.

As such, there remains a need for a stimulation system and method that activates the diaphragm muscle in humans by stimulating the phrenic nerve in a reliable, non-invasive manner. There is a further need to stimulate the phrenic nerve without recruiting somatic pain receptors and without eliciting extraneous muscle contractions. There is another need to provide stimulation to the phrenic nerve in a cost-effective manner. In addition, there is a need for a phrenic nerve stimulation system and method that is widely accessible to clinicians.

In another instance, persons with obstructive sleep apnea need assistance with breathing during periods of sleep. The most common method of treating sleep apnea is with the use of a device that applies continuous positive airway pressure. However, this requires that the person wear a face mask or the like, which for some persons is unacceptable. Thus, there remains a need for a stimulation system and method that causes breathing in humans by stimulating the hypoglossal nerve in a reliable, non-invasive manner.

In another instance, persons suffering from bronchoconstriction (i.e., asthma; COPD) or headache conditions (i.e., migraine; cluster migraine) need adequate acute and/or prophylactic treatment options. Initial studies suggest that vagal nerve stimulation can mitigate or abolish asthma, COPD and a variety of headache types. Therefore, there is a need for a stimulation system and method to activate the vagus nerve non-invasively, without co-activating the surrounding sensitive structures.

SUMMARY OF THE DISCLOSURE

In accordance with one embodiment of the present invention, there is a system for delivering an electrical nerve stimulation through the intact skin of a mammal to stimulate an underlying target nerve. The system includes an electrode ensemble that includes a cathode and an anode. The cathode defines a generally uniform skin contacting surface, where the skin contacting surface of the cathode has an area of from about 1.5 mm² to about 40 mm². Further, a skin contacting surface of the anode has an area that is the same as or larger than the area of the skin contacting surface of the cathode. An electronic control system is electrically attached to each electrode. The electronic control system delivers electrical stimulation through the electrodes to stimulate the target nerve underlying the one or more electrodes without eliciting a pain sensation.

In one aspect, the system can include a component for monitoring a physiological function of the mammal, wherein delivery of the electrical nerve stimulation is coordinated with the physiological function. The physiological function can be, for instance, a respiratory cycle.

In an additional aspect, the electrical nerve stimulation has a constant current of about 0.1 mA to about 20 mA.

In another aspect, the electrical nerve stimulation may be delivered in a single pulse, or in multi-pulse fashion. Multi-pulse stimulation may be applied at a frequency ranging from about 1 Hz to about 45 Hz. The electrical nerve stimulation can also include a carrier frequency ranging from about 1 kilohertz to about 1 megahertz. The electrical nerve stimulation can be a current having a square-wave pulse, and a pulse train that varies in amplitude and frequency. The square-wave pulse can have a pulse-duration of less than about 250 μs. The square-wave pulse can have an inter-pulse interval of less than about 66.5 μs, and can be monophasic and/or ramped.

In an additional aspect, the target nerve can be a phrenic nerve, a vagal nerve, or a hypoglossal nerve. Further, when the target nerve is the phrenic nerve, electrical nerve stimulation of the phrenic nerve can strengthen a diaphragm muscle of the mammal to facilitate waning of the mammal off a ventilator.

In a further aspect, the cathode can have a generally uniform skin contacting surface that can generally be hemispherical, hemispheroidal, ellipsoidal, or the like. In one particular embodiment, the skin contacting surface of the cathode can have an area of from about 3.5 mm² to about 20 mm².

In still another aspect, the electrode ensemble can be either monopolar or bipolar.

In one more aspect, the cathode can include a head and a shaft, where a hood of a shroud device can partially cover the head and a neck of the shroud device can partially cover the shaft. Further, the hood can be configured to rotate around the head to facilitate direction of the electrical nerve stimulation to the target nerve.

In one aspect, the cathode and the anode can be attached to a collar or wrap in a spaced-apart configuration.

In yet another aspect of the disclosure, a method for delivering an electrical nerve stimulation through the intact skin of a mammal to elicit nerve signal transmission in an underlying target nerve is contemplated. The method includes the steps of: locating a target nerve; positioning a cathode on the skin over the target nerve, where the cathode defines a generally uniform skin contacting surface having an area of from about 3.5 mm² to about 40 mm²; positioning a corresponding anode on the skin adjacent the cathode; and delivering electrical nerve stimulation through the cathode to elicit nerve signal transmission in the target nerve underlying the cathode without eliciting a pain sensation.

In one aspect, the method can further include the step of monitoring a physiological function of the mammal, where delivering the electrical nerve stimulation includes coordinating the electrical nerve stimulation with the physiological function. In one instance, the physiological function can be a respiratory cycle.

According to the method, the electrical nerve stimulation may have a constant-current of about 0.1 mA to about 20 mA, and may have frequency ranges from about 1 Hz to about 45 Hz. Further, the electrical nerve stimulation may be constant-current square-wave pulses delivered in a pulse train that is ramped from a starting amplitude of less than about 3 mA to a greater amplitude.

In another aspect of the method, the target nerve can be a phrenic nerve, a vagal nerve, or a hypoglossal nerve. When the target nerve is the phrenic nerve, electrical nerve stimulation of the phrenic nerve can strengthen a diaphragm muscle of the mammal to facilitate weaning of the mammal off a ventilator.

In still another aspect of the method, the anode can have a skin contacting surface that has an area that is the same as or larger than the area of the skin contacting surface of the cathode.

In one more aspect of the method, the cathode can include a head and a shaft, wherein a hood of a shroud device partially covers the head and a neck of the shroud device partially covers the shaft. In one particular embodiment, the hood can be rotated around the head to facilitate direction of the electrical nerve stimulation to the target nerve.

In yet another aspect of the method, the cathode and the anode can be attached to a collar or wrap in a spaced-apart configuration.

In another aspect of the method, a single pulse of electrical stimulation can be delivered to the target nerve prior to the step of delivering electrical nerve stimulation through the cathode and the anode.

In a further aspect, a kit is provided for an electrical nerve stimulation procedure, the kit including one or more cathodes. Each cathode defines a generally uniform skin contacting surface, the skin contacting surface of each cathode having an area of from about 3.5 mm² to about 40 mm². The kit also includes one or more anodes, each anode having a skin contacting surface. The skin contacting surface of each anode has an area that is the same as or larger than the area of the skin contacting surface of each cathode; and electrical leads for connecting the one or more cathodes and the one or more anodes to an electronic control system for delivering electrical stimulation through the one or more cathodes to stimulate a target nerve underlying the one or more cathodes without eliciting a pain sensation.

In one aspect of the kit, the cathode includes a head and a shaft, where a hood of a shroud device partially covers the head and a neck of the shroud device partially covers the shaft. The hood can be configured to rotate around the head to facilitate direction of the electrical nerve stimulation to the target nerve.

There are many advantages of the system, method, and kit of the present disclosure, one being that the technology can be used to not only restore diaphragm muscle health, but it can also be used to prevent atrophy in patients on mechanical ventilation.

Other features and aspects of the present invention are set forth in greater detail below.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DEFINITIONS

Figure 1:
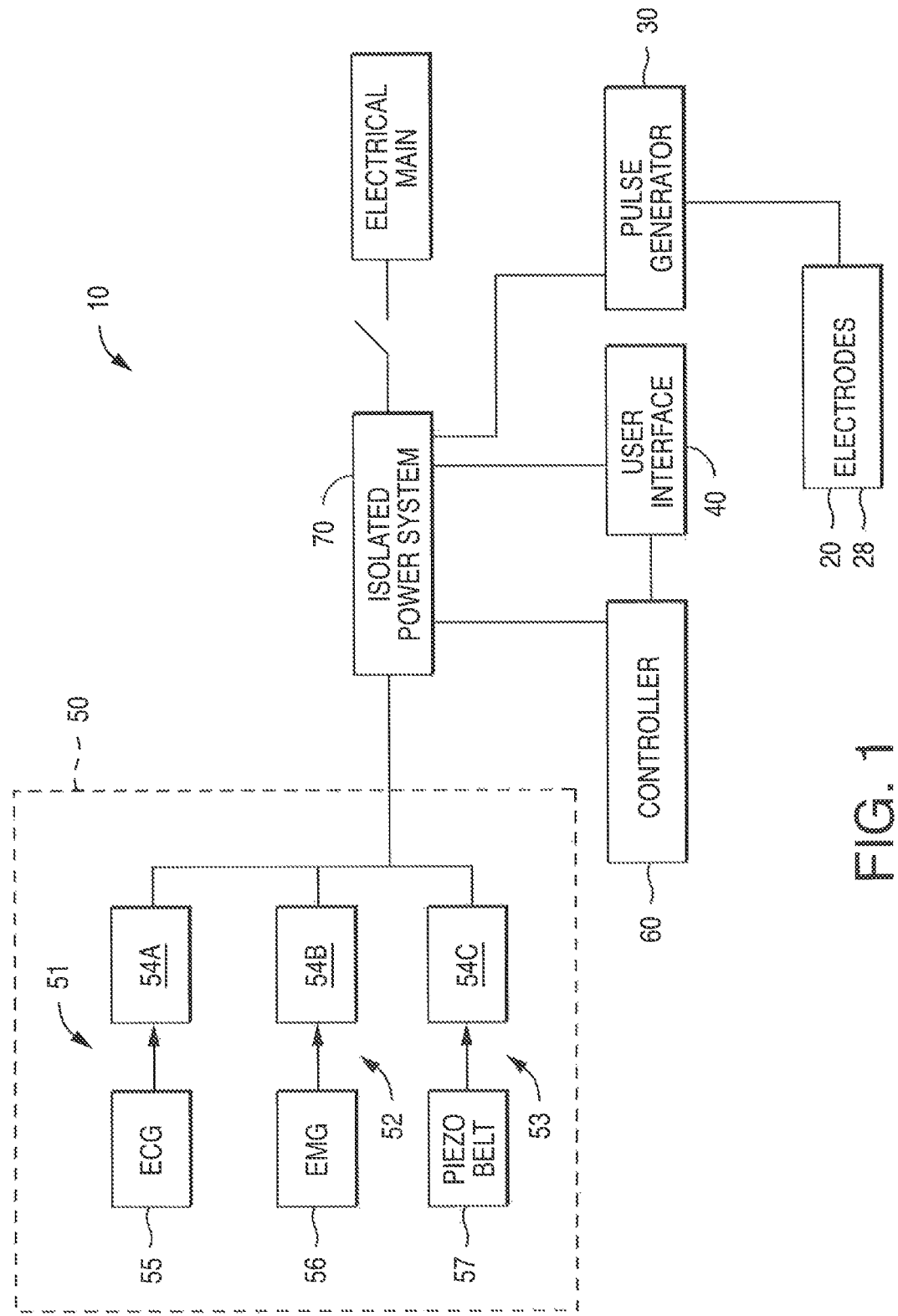
FIG. 1 is a schematic diagram of one embodiment of a stimulation system in accordance with the present disclosure.

As used herein, the terms "carrier frequency", "carrier signal" or "carrier wave" refer to a waveform that has a fixed center frequency that has been modulated (i.e., altered) in a way that its amplitude, frequency, phase or some other property varies. The frequency is measured in Hertz (cycles per second). For purposes of the present invention, a carrier frequency is selected to provide low skin impedance and to carry a modulating frequency. Desirably, a carrier frequency is a high frequency waveform.

As used herein, the term "disposable" refers to a product that is so inexpensive that it may economically be discarded after only a single use. Products that are "disposable" are typically intended for single use. The term "single-use" refers to a product that is intended to be used for only once and is not intended to be re-used, re-conditioned, restored or repaired after that use. These products offer advantages in clinical settings by reducing the potential for contamination or infection. In addition, these products can enhance work flow since they are not collected and assembled for reprocessing and reuse. As desired, the cathodes and anodes of the present disclosure may be disposable.

As used herein, the term "intact skin" refers to skin that is sound, unbroken and uninjured, or not altered in any meaningful way such as, for example, by fresh surgical incision, fresh piercing by an instrument such as a needle, trocar or the like.

As used herein, the terms "pain sensation" or "painful sensation" refers to a highly disagreeable sensation generated by the activation of sensory nociceptors. Nociception describes the perception of acute pain.

DETAILED DESCRIPTION OF THE DISCLOSURE

Reference now will be made in detail to various embodiments of the disclosure, one or more examples of which are set forth below. Each example is provided by way of explanation, not limitation of the disclosure. In fact, it will be apparent to those skilled in the art that various modifications and variations may be made in the present disclosure without departing from the scope or spirit of the invention. For instance, features illustrated or described as part of one embodiment, may be used on another embodiment to yield a still further embodiment. Thus, it is intended that the present invention cover such modifications and variations.

Disclosed is a system for delivering electrical nerve stimulation through the intact skin to stimulate an underlying target nerve. Generally speaking, the intact skin is intact mammalian skin. According to the invention, the electrical stimulation is delivered transcutaneously without use of an instrument or electrode that physically penetrates the skin by incision, piercing, or the like to be physically adjacent the target nerve. In other words, electrical stimulation is delivered directly to intact skin to stimulate an underlying target nerve in a non-invasive manner.

In one aspect of the present disclosure, an electrical stimulation system and corresponding method are used to induce a muscle contraction of the diaphragm via transcutaneous electrical stimulation of a target nerve, which is the phrenic nerve. For instance, the cathodic electrode having a small head (less than 7 mm diameter) is placed in the proximity of a phrenic nerve. The cathode is part of an electrode ensemble (i.e., a cathode and an anode) used to electrically stimulate the nerve with short electrical pulse durations of 50 µs to 150 µs, at frequencies of 1 Hz to 45 Hz. The current is controlled at about 0.1 mA to 20 mA. This electrical stimulation elicits a diaphragm muscle contraction without any pain sensation or extraneous muscle movements.

Constant-voltage nerve stimulation elicits variable amounts of current. As the skin or electrode impedance increases, the amount of current decreases. When the impedance increases in a constant-current device, the voltage increases automatically to maintain the desired current output. Either a constant voltage or current may be used, though the constant-current device is a more desirable way of stimulating a nerve.

The stimulation method can reliably elicit the phrenic nerve in humans that are awake, causing diaphragm muscle contraction. As described previously, repeated diaphragm muscle contractions enable the muscle to strengthen and become more functional (i.e., similar to weightlifting). The methodology can be used to more easily wean a person from ventilator support through periodic treatments. Altogether, the stimulation will strengthen a person's diaphragm muscles, enabling them a shorter hospital stay and a healthier discharge. Just one of the several advantages which will be apparent throughout the present disclosure is that the time required to wean a patient off of respiratory assistance by the disclosed method can be significantly shortened when compared to prior methods.

The method of the present disclosure may also be used to prevent atrophy of the diaphragm muscle. More specifically, atrophy prevention could be the result of conjoining the stimulation system with the respiratory assistance equipment so that the electrical stimulation of the nerve is phase-locked with the respirator.

In another aspect of the present disclosure, the system and method of the present disclosure may be used to treat central sleep apnea by stimulating the phrenic nerve, or obstructive sleep apnea by stimulating the hypoglossal nerve. In this aspect, after a certain period of apnea is detected by a sensor, stimulation of the targeted nerve is used to elicit diaphragm muscle contraction.

A practical use of the above-noted respiratory treatment is during surgical or other medical procedures where it is necessary to retard the central nervous system (e.g., through trauma, the application of anesthesia or narcotics), and where the patient maintains a substantially constant position. Other practical uses of the treatment include: 1) disrupting idiopathic chronic hiccups; 2) preserving diaphragm health in persons with amyotrophic lateral sclerosis (ALS) or spinal cord injury; and 3) strengthening an already healthy diaphragm in persons preparing for extreme respiratory challenges (i.e., sporting events, singing).

Stimulation System

In one aspect of the present disclosure, the electrical stimulation system includes multiple devices to sense, control and deliver predetermined electrical pulses to targeted nerve(s). In general, the system, referenced as the schematic system 10 in FIG. 1, may include an electrode ensemble (cathode 20 and anode 28), a pulse generator 30, a user interface 40, a patient monitor system 50, a controller 60, and an isolated power system 70. While an experimental-scale system is shown and described, it is contemplated that a more compact unit could be used to control and deliver the desired electrical stimulation.

Stimulating Electrode

Figure 2A:
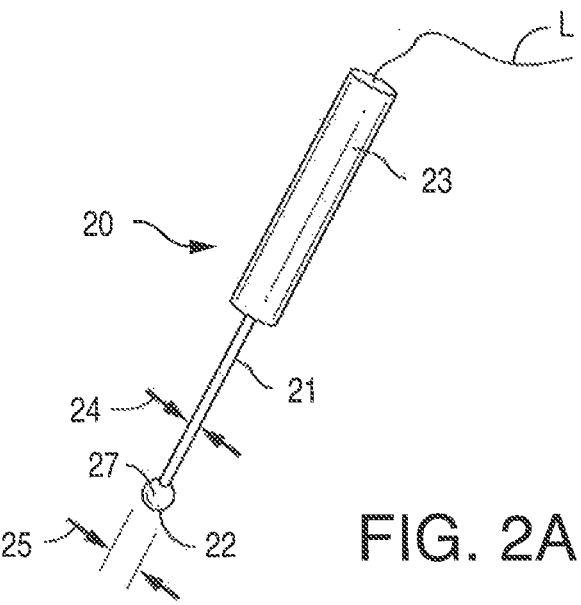
FIG. 2A is a perspective side view of one embodiment of a stimulation electrode of the present disclosure.

Referring to FIG. 2A, the overall shape of the stimulating electrode otherwise referred to as the cathode 20, is such that it allows an operator to precisely place the cathode head 22 in the proximity of a targeted nerve. In one aspect of the disclosure, the cathode 20 includes an elongated shaft 21 having a head 22 at one end, and a support such as a handle 23 at the opposite end. The cathode head 22 has a blunt shape, as described. The shaft diameter 24, for a distance of at least about one inch from the head 22, is less than or equal to the head diameter 25. An electrical lead L may be integrated with cathode 22 or attached using a conventional electrical connector. One possible cathode that meets such criteria is a pedical screw probe, model PSP-1000, available from Axon Systems, Inc., NY.

Generally speaking, the cathode head 22 defines a generally uniform skin contacting surface. That is, the skin contacting surface should avoid protuberances, sharp edges, points or features that may undesirably concentrate current passing from the electrode or even pierce the skin.

Desirably, the skin contacting surface of each cathode head 22 has an area of from about 1.5 mm$^2$ to about 40 mm$^2$. Desirably, the skin contacting surface 27 has an area of from about 3.5 mm$^2$ to about 20 mm$^2$.

Cathode head 22 may have an oval, elliptical or circular cross-section. Desirably, head 24 of the cathode 20 is circular and may be about 2.5 mm to about 7 mm in diameter; or about 2.5 mm to about 5 mm in diameter, or most desirably is about 2.5 mm diameter.

In one aspect of the present disclosure, the head 22 of cathode 20 has a spherical shape and is less than about 7 mm in diameter; or less than about 5 mm in diameter, or most desirably about 2.5 mm diameter. These sizes are such that the head 22 can fit between desired muscles adjacent the target nerve.

A head 22 that is too large will not only fail to fit between the muscles adjacent to the target nerve, but will have a low current density as compared to a relatively small head 22 ("small" as described above). If the current density is too low to achieve the desired diaphragm response, more power must be delivered to the electrode thereby increasing the potential for discomfort. Further, a small head 22 is less likely to activate the skin's pain receptors and is more controllable so it is easier to position the probe over top of the target nerve without co-activating nearby excitable tissues.

Figure 2B:
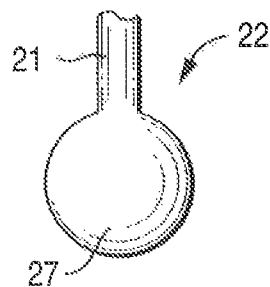
FIGS. 2B, 2C, 2D, and 2E are perspective side views of various embodiments of electrode heads according to the present disclosure.
Figure 2C:
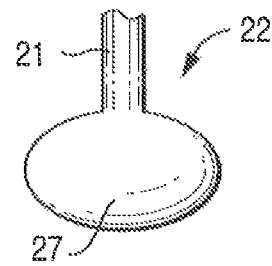
Figure 2D:
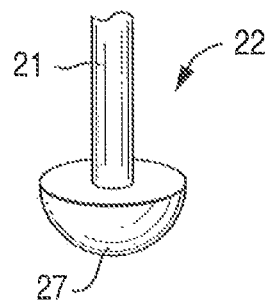

FIG. 2A is an illustration of an exemplary cathode head 22 extending from the shaft 21. Head 22 has a generally spherical shape to provide a generally uniform skin contacting surface 27. FIG. 2B is an illustration of another exemplary head 22 extending from shaft 21. Here, head 22 has a generally spheroidal shape (e.g., an oblate spheroid) to provide a generally uniform skin contacting surface 27. FIG. 2C is an illustration of yet another exemplary head 22 extending from shaft 21. Head 22 has a generally hemi-spherical shape to provide a generally uniform skin contacting surface 27. FIG. 2D is an illustration of still yet another exemplary head 22 extending from the shaft 21. Here, head 22 has a generally hemispheroidal shape (e.g., about one-half of an oblate spheroid) to provide a generally uniform skin contacting surface 27. Of course, it is contemplated that a variety of other shapes and configurations may be utilized provided that the skin contacting surface avoids protuberances, sharp edges, points or features that may undesirably concentrate electrical current passing from the electrode or pierce the skin.

In one aspect of the disclosure, the shaft 21 is coated with TEFLON fluoropolymer or other insulating material to better control current delivery and the electrode's impedance. The relatively small cathode head 22 corresponds to a relatively large current density of about 12.5 mA/cm$^2$, to about 9.5 mA/cm$^2$, and most desirably, to 3.5 mA/cm$^2$. As the exposed area of the cathode head 22 decreases, the current density increases unless there is less power delivered to the cathode.

In one aspect of the present disclosure, the head 22 is constructed from a metal that is biocompatible, such as stainless steel. The handle 23 is large enough for a clinician to comfortably grip, and is made of a material that will minimize the risk of accidental shock (e.g., plastic).

Figure 13:
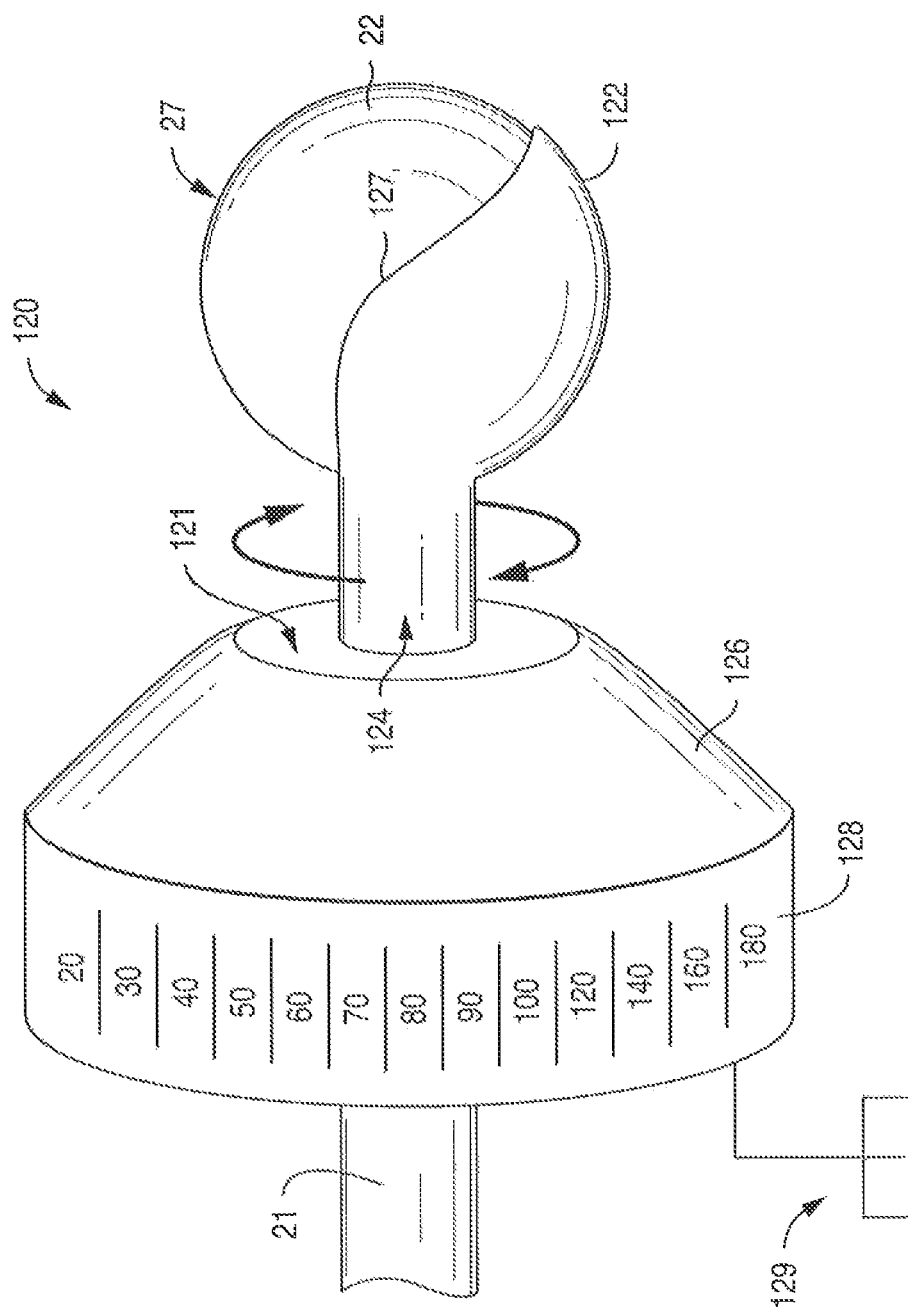
FIG. 13 is a side perspective view of one embodiment of an adjustable shroud positioned on a cathode according to the present disclosure.
Figure 14:
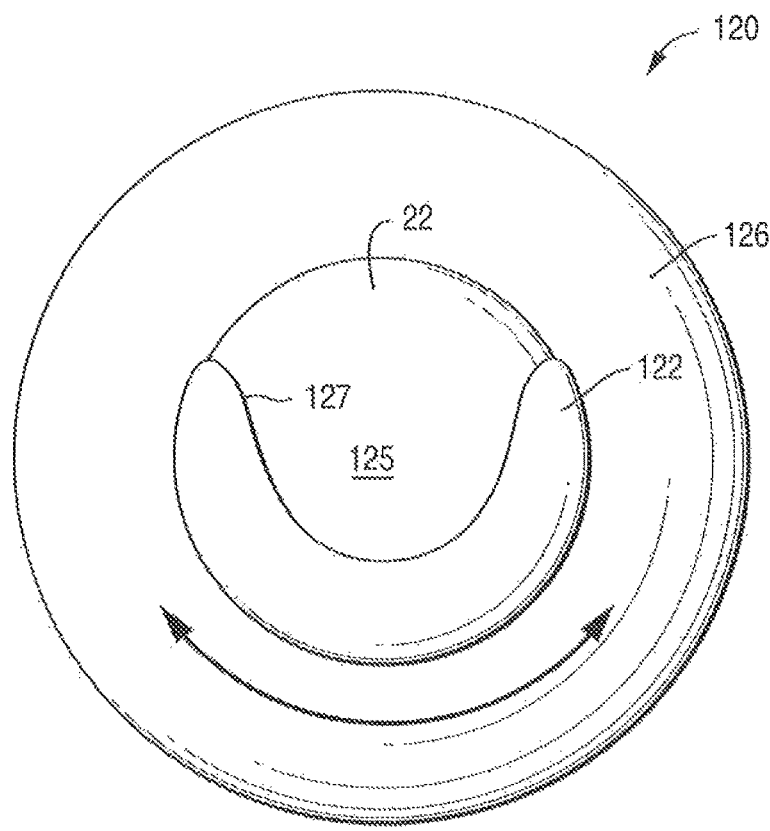
FIG. 14 is a plan view of the adjustable shroud of FIG. 13.

In one aspect of the disclosure, a shroud device 120 is used to partially cover the head 22 allowing the user to direct current toward a target nerve more effectively. Referring to FIGS. 13 and 14, the shroud device 120 includes a hood 122 that partially covers head 22, and a neck 124 that may completely cover shaft 21 extending from head 22. Hood 122 electrically insulates the cathode to prevent current from travelling from head 22 beyond hood 122.

Hood 122 wraps around about one-third to one-half of head 22, and is cup-shaped so that it fits closely to the conductive surface 27 of head 22. Desirably, the top surface 125 (see FIG. 14) is partially exposed so that the user does not have to hold the shaft 21 against the patient's body to direct head 22 at the target nerve.

Hood 22 may be made from insulative materials such as TEFLON-coated metal or other non-conductive materials. Hood 122 is either static (possibly applied as a coating) or rotatable. A rotatable hood 122 and neck 124 fits closely around head 22 yet during rotation, experiences a negligible amount of friction between head 22 and hood 122, and shaft 21 and neck 124. Desirably, the edge 127 of hood 122 is smooth so that it does not cause discomfort to the patient as the head 22 is pressed against the skin.

In another aspect of the disclosure, a shoulder 126 may be used to provide the user with a convenient way to rotate the hood 122 around head 22. Referring to FIG. 13, one exemplary shoulder 126 may have a truncated cone-shape with a trunk 128 extending therefrom in a direction away from hood 122. The transition between the shoulder 126 and trunk 128 may be smooth and not be a hard edge as depicted. To the center of the shoulder 126, on a surface 121 opposite the trunk 128, the neck 124 is attached.

Trunk 128 may be used as a dial to rotate hood 122 about head 22. Trunk 128 may be marked with numerical indicators describing the head's 22 position with respect to the body. It is noted that the current flows from a cathode to its corresponding anode, and the target nerve is located in-between. The insulated hood enables the current flow to be better directed (i.e., anteriorly vs. posteriorly). For example, if the target nerve is a phrenic nerve, one may rotate the hood directing the current toward the phrenic nerve. If one were to turn hood 122 about 180 degrees, the brachial plexus, which is located posteriolaterally to the phrenic nerve at Erb's point, would instead be stimulated.

Shoulder 126 is grounded by a ground 129, and made from a material that will shield or prevent current from spreading on the surface of the skin.

Figure 3:
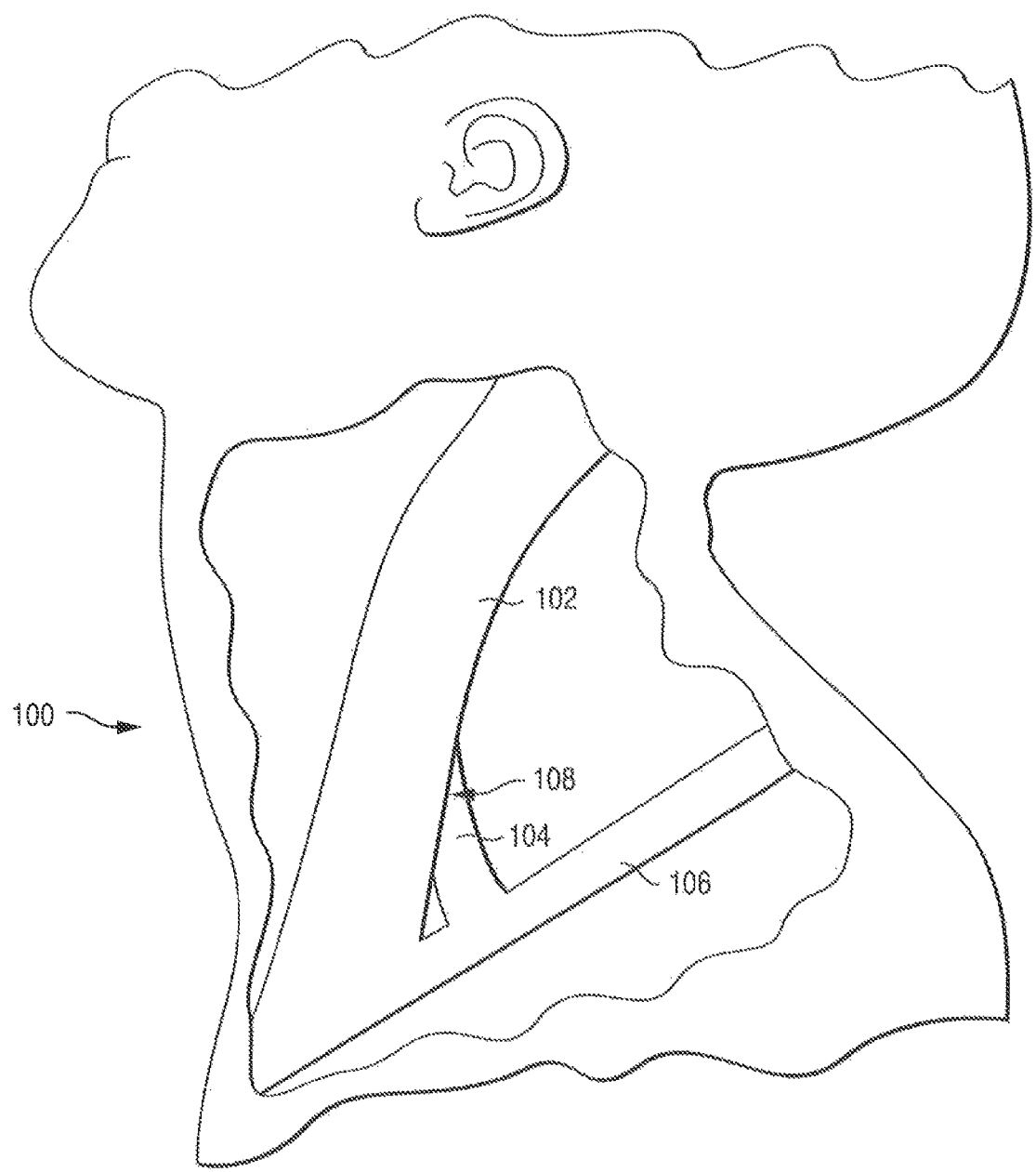
FIG. 3 is a cutaway view of a human neck showing the sternocleidomastoid muscle, the scalenus anterior muscle and the general location of the phrenic nerve.

Another possible advantage to using the optional shoulder 126 in the example of phrenic nerve stimulation is that when pressed against the skin, it helps separate the sternocleidomastoid muscle 102 from the scalene anterior muscle 104 for easier access to the phrenic nerve (see FIG. 3), which descends on the anterior surface of the scalene muscle. This concept may apply to other muscles adjacent other target nerves.

Figure 15:
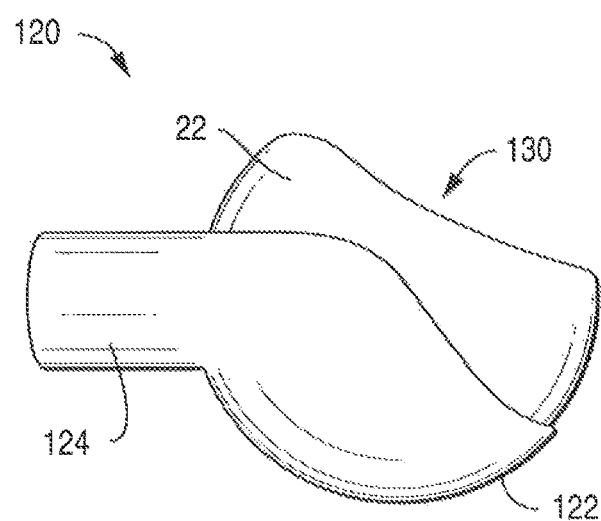
FIG. 15 is a side elevation of another embodiment of an adjustable shroud positioned on a cathode with a contoured head.

It is noted that the shroud 120 may be used in conjunction with an asymmetrical head 22. For example, shown in FIG. 15 is a contoured head 22 that is generally an egg-shape with a concave portion 120. This shape may be desirable for focusing current onto a target nerve, e.g., the phrenic nerve.

Figure 11:
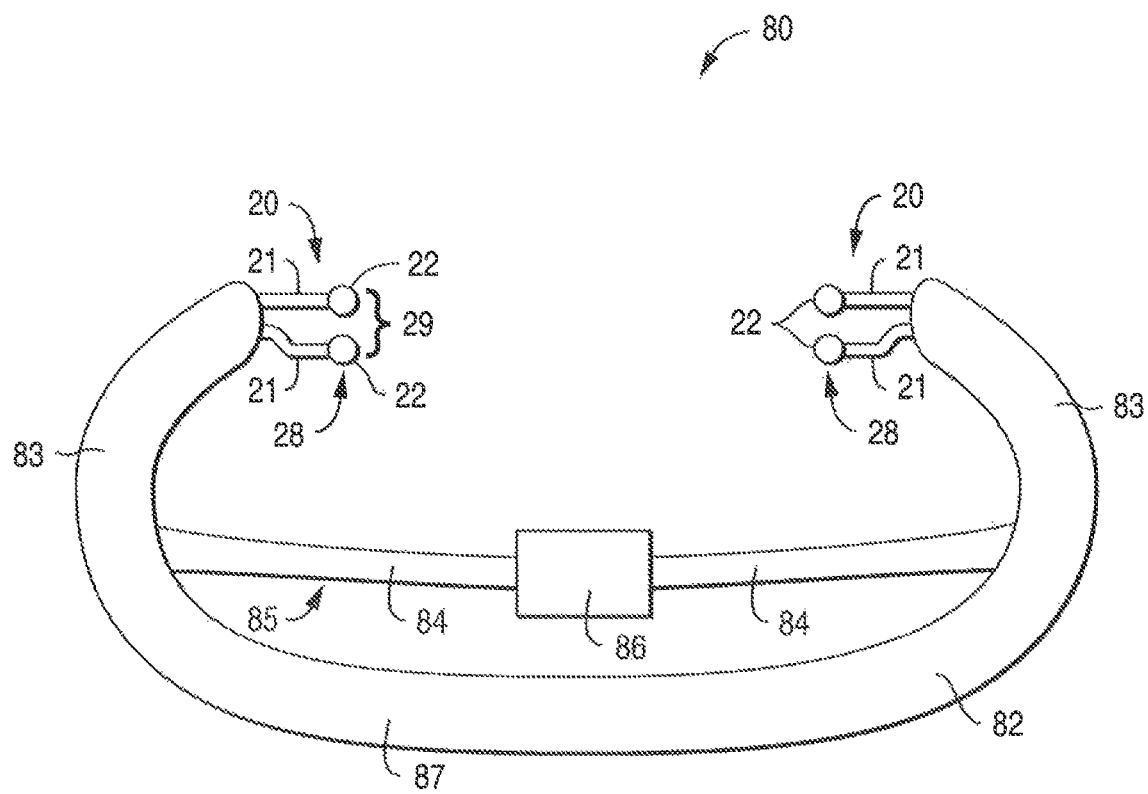
FIG. 11 is another embodiment of a holding device of the present disclosure.

In another aspect of the disclosure (referring now to FIG. 11), it is contemplated that the shaft 21 may be truncated to the head 22 (leaving only a small portion of shaft 21) and attached to a holding device that can securely position the electrode over the targeted nerve during the nerve stimulation procedure. For example, FIG. 11 shows one embodiment of a holding device, collar 80, to which cathodes 20 and anodes 28 are attached; there is one anode 28 for every cathode 20. Designed for phrenic nerve stimulation, collar 80 has a C-shaped body with a pair of arms 83. Anodes 28 and cathodes 20 are attached to the end of arms 83. Desirably, the shafts 21 of each cathode 20 are generally aligned along their respective longitudinal axes so that heads 22 are directed toward each other. The shafts 21 of each anode 28 are bendable or otherwise adjustable because desirably, the inter-electrode distance 29 between the heads 22 of a cathode 20 and corresponding anode 28 is adjustable and maintainable at a distance greater than 0.5 cm. Furthermore, the anode 28 may be placed on the superior aspect of the clavicle, about 3 cm caudal to the cathode 20.

Between arms 83 is a trunk member 87, which serves to connect the base of each arm 83, opposite the electrodes. A bridge 85 spans between the arms 83, and is used to adjust the tension between the two sets of electrodes so that the collar 80 will not slip out of place during use. The bridge 85 is constructed from a pair of tension brackets 84 aligned along their respective longitudinal axes and connected to one another by a tensioning device 86. The tensioning device may be any mechanism that can selectively draw tension brackets 84 together.

Figure 12:
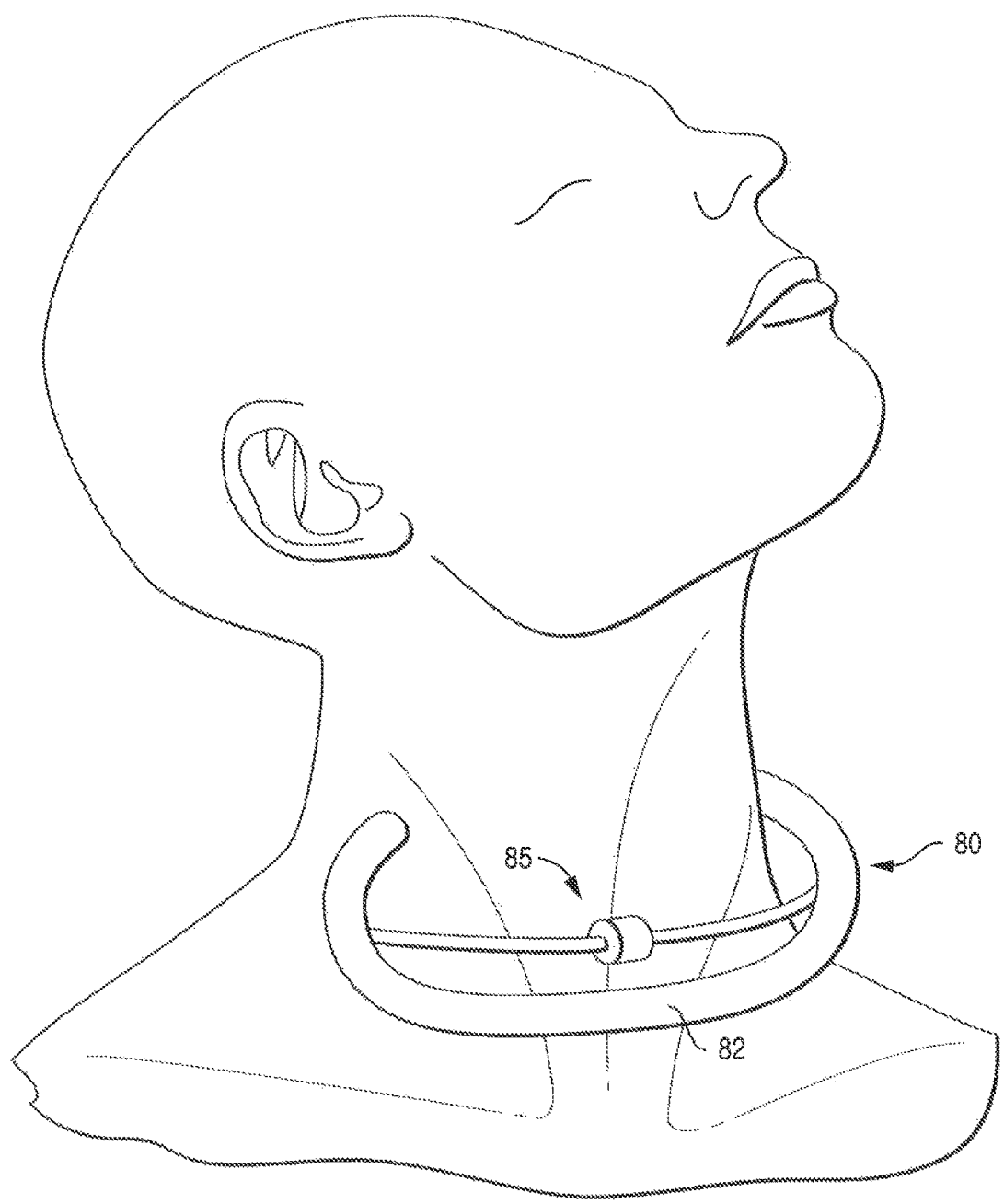
FIG. 12 is a depiction of where the holding device of FIG. 11 may be positioned on a human neck.

FIG. 12 illustrates how collar 80 may be positioned so that bilateral stimulation of the phrenic nerves may be obtained. Generally, the cathode heads 22 are positioned against the phrenic nerve on each side of the neck. See FIG. 3 which illustrates the neck 100 of a subject, in which the phrenic nerve 108 may be accessed above the clavicle 106, and between the sternocleidomastoid muscle 102 and the scalenus anterior muscle 104.

Figure 10:
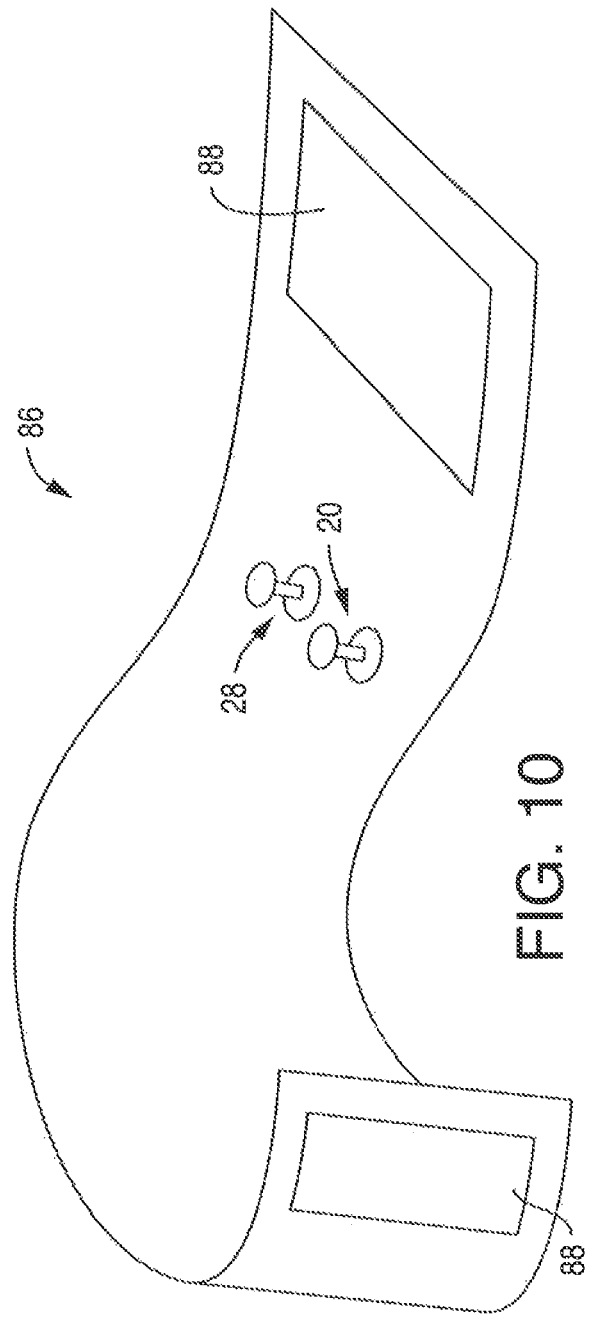
FIG. 10 is one embodiment of a holding device according to the present disclosure.

In another aspect of the disclosure, the holding device is a strap 86 having at least one cathode 20 and anode 28. See, FIG. 10. The strap may have fastening components 88 such as, for example, cohesive materials or mechanical fasteners (e.g., hook & loop systems, clips, snaps, pins, etc.).

One type of anode 28 is constructed similarly to the cathode. In one aspect of the present disclosure regardless of embodiment, the anode's skin contacting surface 27 has the same surface area as the skin contacting surface of the cathode. In other aspects of the present disclosure, anode 28 has a larger skin contacting surface than that of cathode 20.

The electrode ensemble may deliver stimulation in monopolar fashion or mode. In this monopolar mode, one or more cathodes are positioned over the target nerve and a second dispersive electrode (anode) with a relatively larger surface area is positioned on a surface of the patient's body to complete the circuit. Alternatively, the stimulation may be delivered in a bipolar fashion or mode and the above-described system may further include one or more anodes. When the stimulation is delivered in a bipolar fashion or mode, the cathode(s) is positioned over the target nerve and the corresponding anode(s) is positioned on the skin over the target nerve to preferentially concentrate the delivery of electrical energy between each cathode and anode. In the bipolar mode, the anode(s) should be positioned a sufficient distance away from the cathode(s) to avoid shunting. The skin contacting surface of each anode will desirably have at least the same or greater surface area as the skin contacting surface of each corresponding cathode.

Pulse Generator

Referring again to FIG. 1, in one aspect, the electrode ensemble (cathode 20 and anode 28) may be electrically connected via a lead wire to a pulse generator 30. The pulse generator 30 is a constant-current stimulator. One exemplary stimulator is the constant current DIGITIMER DS5 peripheral electrical stimulator available from Digitimer Ltd., England. The Digitimer DS5 machine delivers a bipolar stimulation. In another aspect of the present disclosure, pulse generator 30 may be a constant-voltage pulse-generator. For example, three such generators are available from Grass Technologies, a subsidiary of Astro-Med, Inc., RI, US, as models S88X, S48, SD9. Monopolar stimulation will also activate a target nerve and cause muscle contraction, but with lesser effectiveness.

User Interface

User interface 40 is a computer that operates software designed to record signals passed from the controller, and to drive the controller's output. Possible software includes Cambridge Electronic Design's (UK) "SPIKE" program. The software is programmable and can record and analyze electrophysiological signals, as well as direct the controller to enable stimulation.

Patient Monitoring System Used for Phrenic Nerve Stimulation

The patient monitoring system 50 collects, amplifies and filters physiological signals, and outputs them to the controller 60. The acquired outcome measures include: 1) heart-rate 51, 2) muscle activity 52, and 3) respiration 53. Electrocardiogram and electromyography signals from the heart and diaphragm muscle respectively, are recorded by surface electrodes. Respiration may be measured mechanically by a strain-gauge respiratory belt transducer that is wrapped around the patient's chest. All physiological signals obtained with the patient monitoring system are passed through an AC signal amplifier/conditioner (54A, 54B, 54C). One example of an amplifier/conditioner is the Model LP511 AC amplifier available from Grass Technologies, a subsidiary of Astro-Med, Inc., West Warwick, R.I., USA. Electromyogram activity recorded from the diaphragm muscle and others will be paired to the controller to help the device optimize its calibration and stimulation paradigm, and indicate its effectiveness and specificity to the caregiver.

Controller

The controller 60 performs data acquisition functions by acquiring electrophysiological waveform data from the signal amplifiers/conditioners 50, and outputs electrical signals for real-time control of the pulse generator 30. The controller 60 may have onboard memory to facilitate high speed data capture, independent waveform sample rates and on-line analysis. In one aspect, the controller 60 may be a POWER 1401 data-acquisition interface unit available from Cambridge Electronic Design, UK.

Isolated Power System

All instruments are powered by an isolated power supply or system 70 to protect them from ground faults and power spikes carried by the electrical main. An exemplary isolated power system is available is the Model IPS115 Isolated Medical-grade Power System from Grass Technologies, a subsidiary of Astro-Med, Inc., West Warwick, R.I., USA.

While not bound to a particular theory of operation, it is generally believed that by using a stimulating electrode on the surface of the skin that is substantially smaller than typical skin-contacting stimulating electrodes, the amount of current needed to stimulate a nerve or nerve fiber can be reduced, particularly when a carrier frequency is utilized. The amount of current can be minimized at least because the current density is focused which avoids generating pain sensations. Having sufficient current density to provide nerve stimulation as well as a relatively low power density will prevent pain sensations.

The carrier frequency enables a better energy transfer through the skin, so that modulating stimuli can more easily affect the underlying nerves. The FDA recommends that power calculations for transcutaneous stimulation use a skin impedance of 500Ω. Studies show that the use of carrier frequencies up to 1 MHz can reduce the skin's impedance to 100Ω. Accordingly, if the present invention utilizes an electrode having a diameter of approximately 2.5 mm (Area 0.05 cm² or A) to deliver electrical stimulation at 25 kHz (DC; square-wave) and 10 milliamps (Ipeak), then the power density (PD; Eqn. 1) used to deliver the same current (140 milliamps/cm²) to the nerve is reduced by a factor of 5. The application of a carrier frequency would reduce the resulting power density from 500 mW/cm² to 100 mW/cm² if the same current density is applied to the nerve.

$$PD = ((I_{rms}^2 \times \Omega))/A \qquad \text{Eqn. 1:}$$

$$I_{rms} = I_{peak}(\sqrt{DC}) \qquad \text{Eqn. 2:}$$

Figure 2E:
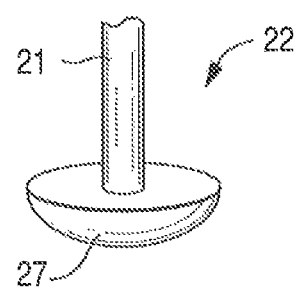
Figure 8:
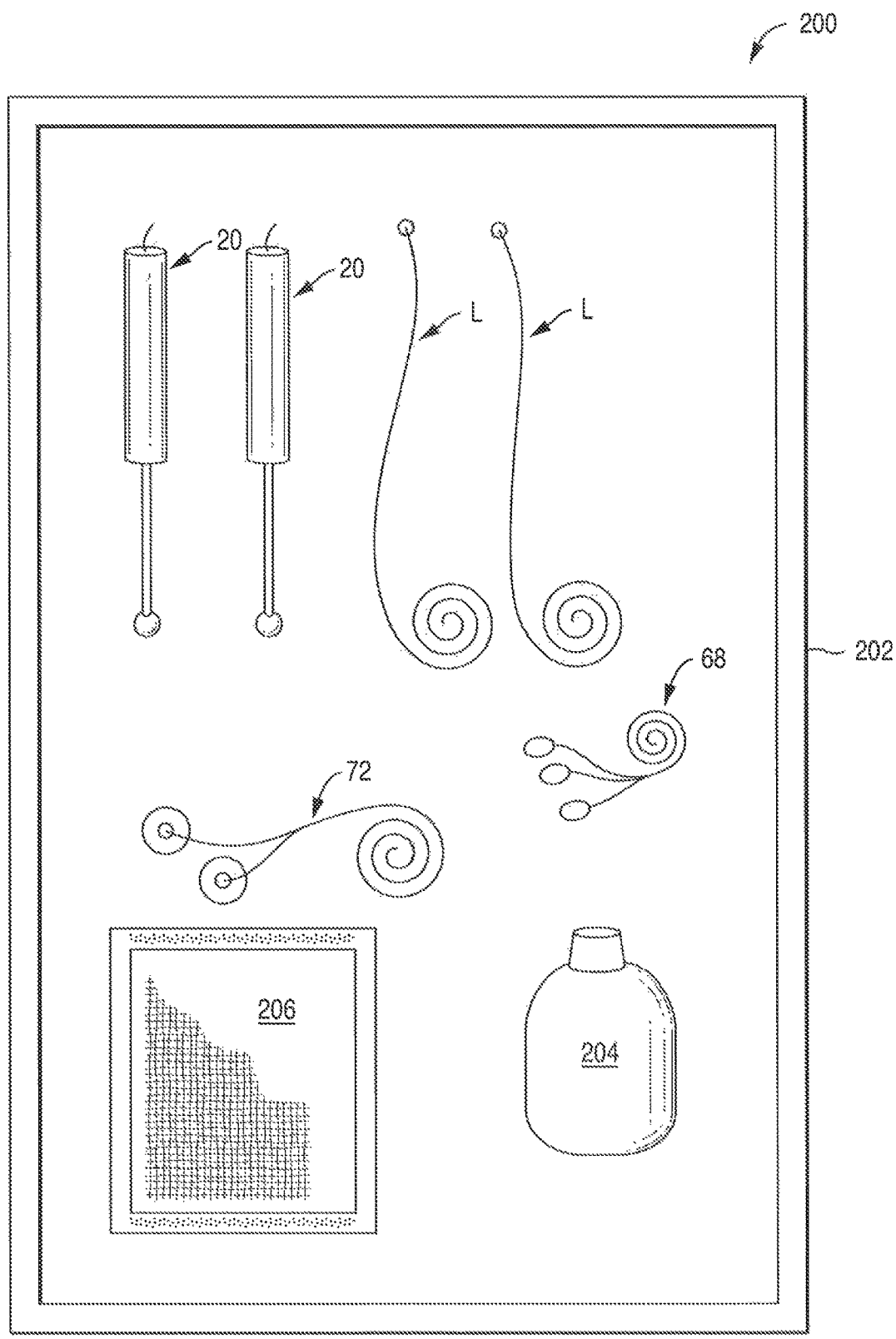
FIG. 8 is a plan view of a kit in accordance with one embodiment of the present disclosure.

The present invention also encompasses a kit for an electrical stimulation procedure. FIG. 8 depicts a kit 200 that includes any manner of suitable container 202 in which is provided any combination of the components depicted in FIG. 1 through FIG. 2E and possibly, FIGS. 10-15. It should be appreciated that the kit 200 need not contain all of the articles depicted in FIG. 1. That is, components such as controller, pulse generator, user interface, patient monitoring system amplifiers or the like need not be included.

The container 202 may be, for example, a suitable tray having a removable sealed covering in which the articles are contained. For example, an embodiment of the kit 200 may include the container 202 with one or more cathodes 20 and electrical leads "L" as discussed above. The kit may further include one or more anodes 28 (not shown).

Other embodiments of a kit 200 may include additional items that are not shown such as ECG electrodes 55, EMG electrodes 56, and piezoelectric belt transducer 57 as well as any combination of a drape, site dressings, tape, skin-markers and so forth. The kit 200 may include one or more containers 204 of electrically conductive liquids or gels, antiseptics, or skin-prep liquids. The kit 200 may include pre-packaged wipes 206 such as electrically conductive liquid or gel wipes, antiseptic wipes, or skin-prep wipes.

Electrical Stimulation Parameters for Phrenic Nerve Stimulation

1. Stimulation type: Constant-current, or constant-voltage square-wave pulse.
2. Waveform: Monophasic, or biphasic.
3. Pulse duration: may be less than about 100 to about 250 µs; or about 100 to about 150 µs; or most desirably 100 µs.
4. Phase duration: (for biphasic pulses only) may be less than about 50 µs to about 125 µs; or about 50 µs to about 75 µs; or most desirably 50 µs for each portion of the pulse.
5. Current: may be about 0.01 mA to 20 mA. The most desirable is a range of 3 mA to 4 mA (or up to 5 mA if the person is very obese).
6. Current density: (amount of current (mA) per unit area (cm²) for a hemispherical, 2.5 mm diameter, electrode head) may be about 12.5 mA/cm², to 9.5 mA/cm² and most desirably, about 3.5 mA/cm².
7. Interpulse intervals: (the time between pulses) may be less than about 66.5 µs; or less than 21.95 µs. The interpulse interval allows for mechanical changes in the muscle tissues such as when eliciting muscle contractions.
8. Pulse period: (the amount of time between the start of one pulse to the start of the next pulse; it includes phase duration, intrapulse intervals, and interpulse intervals) may be less than about 66 ms; or less than about 44 ms; or most desirably about 22 ms. The pulse period is inversely proportional to frequency.
9. Pulse frequency: may be about 1 Hz to 45 Hz, or about 20 Hz to 35 Hz, or most desirably, about 25 Hz. Frequencies of at least 20 Hz result in a fused diaphragm response.
10. Carrier signal: Electrical stimuli can be superimposed onto an optional carrier signal. The carrier signal may be used to lower the skin's impedance during stimulation, reducing the amount of current needed by the modulating frequency described above to activate the nerve. The carrier signal may be delivered in an amplitude-modulated fashion. The carrier signal may be sinusoidal or a square-wave in shape, and be delivered between 1,000 Hz and 1,000,000 Hz (or 1 MHz). The stimulation system may also decide the optimal carrier signal during system start-up, or calibration.

11. Pulse train: Single pulse and multiple pulses will be delivered. A single pulse is used at start-up or calibration to determine stimulation effectiveness and safety. A train of multiple pulses may be delivered for duration of about 1 second, or as needed by the person. Each pulse train is separated by an off time which is the interburst interval. The duration of the pulse train determines the duration of inspiration and is variable between and within subjects. The pulse train enables a smooth inhalation and transition to exhalation. Expiration is passive.

12. Interburst interval: (the off time between each pulse train) is variable and dependent on the patient.

13. Pulse ramp: takes place when the intensity of each pulse is increased or decreased incrementally. Desirably, the ramp begins with a pulse intensity pedestal that is less than is needed to elicit a diaphragm muscle contraction. Eventually, as the intensity is increased, the phrenic nerve's motor threshold is crossed and the diaphragm muscle begins contracting in a physiological fashion. After the intended contraction is produced, then the intensity of each subsequent pulses is decreased incrementally until the respiratory cycle is completed. The pulse ramp is designed for functionality and comfort.

Electrical Stimulation Parameters for Hypoglossal and Vagal Nerve Stimulation

The parameters for the hypoglossal and vagal nerve stimulation are the same for that of the phrenic nerve stimulation.

Electrical Stimulation Method

The present invention also encompasses a method for delivering electrical stimulation through the intact skin to stimulate an underlying target nerve. The method involves the steps of: locating a target nerve; positioning one or more cathodes each with a corresponding anode, on the skin over the target nerve in which each cathode defines a generally uniform skin contacting surface having an area of from about 3.5 mm$^2$ to about 40 mm$^2$; and delivering electrical stimulation utilizing these electrodes to stimulate a target nerve underlying the cathode(s) without eliciting painful sensations or activating ancillary structures (i.e., muscles, non-target nerves).

The separation between the surface of the skin and the target nerve is on the order of millimeters. Mild amounts of pressure may be applied to the stimulating electrode to decrease the electrode-skin distance, reducing the effective stimulation intensity and improve subject comfort.

The method further includes positioning an anode on the skin, one for each corresponding cathode. Desirably, an anode is positioned on the skin over the target nerve at a distance away from the corresponding cathode sufficient to avoid shunting.

Generally speaking, the use of current regulated stimuli has an advantage over voltage regulated stimuli because the stimulation current density is better controlled.

The method of practicing the present invention may further include the use of coupling media such as an electrically conductive liquid, gel or paste that may be applied to the skin to enhance the conductivity of the skin and/or lower impedance. Alternatively and/or additionally, one or more skin moisturizers, humectants or the like may be applied to the skin for the purpose of enhancing the conductivity of the skin and/or lowering impedance of the skin. Examples of conductive pastes include Ten20™ conductive paste from Weaver and Company, Aurora, Colo., and ELE-FIX Conductive Paste from Nihon Kohden with offices at Foothill Ranch, Calif. Examples of conductive gels include Spectra 360 Electrode Gel from Parker Laboratories, Inc., Fairfield, N.J., or Electro-Gel from Electro-Cap International, Inc., Eaton, Ohio.

Phrenic Nerve

In most cases it is desirable to provide bilateral nerve stimulation for maximum efficacy. However, it is possible to stimulate a single hemidiaphragm through its corresponding phrenic nerve. Unilateral nerve stimulation is desirable if one lung or nerve is not operational, such as through surgical removal, collapse or damage.

Bilateral Phrenic Nerve Stimulation Procedure

1. Setup stimulation system near a stable patient bed.
2. Place patient into a comfortable supine position.
3. Place the ECG, EMG and respiratory belt transducer on patient.
4. Begin monitoring respiration, heart-rate and diaphragm EMG signals.
5. Locate the posterior border of the sternocleidomastoid muscle on each side of the patient's neck region.
6. It is most desirable to place a mark on the skin to indicate the desired location of the stimulation electrode placement.
7. For each desired location, position the head of a cathode thereon and apply mild pressure to reduce the distance between the cathode and the phrenic nerve. Maintain the stimulation electrode in this position.
8. For each electrode, position an anode at the superior surface of the clavicle and caudal to the cathode. Deliver a single-pulse of electrical stimulation to the left and right side stimulation site, and use visual and EMG outcomes to verify stimulus-elicited diaphragm muscle contractions.
9. Using the electrical stimulation parameters, apply a rectangular, multi-pulse electrical stimulation to the phrenic nerve bilaterally to achieve a fused diaphragm contraction. The electrical stimulation may be applied to the phrenic nerve simultaneously, or each hemidiaphragm may be stimulated alternately to allow a greater rest period for each.
10. Determine if cardiovascular system is stable by analyzing heart-rate variability and systolic blood pressure. If these measures change appreciably from baseline, then terminate stimulation.

Vagal Nerve Stimulation Procedure

Figure 16:
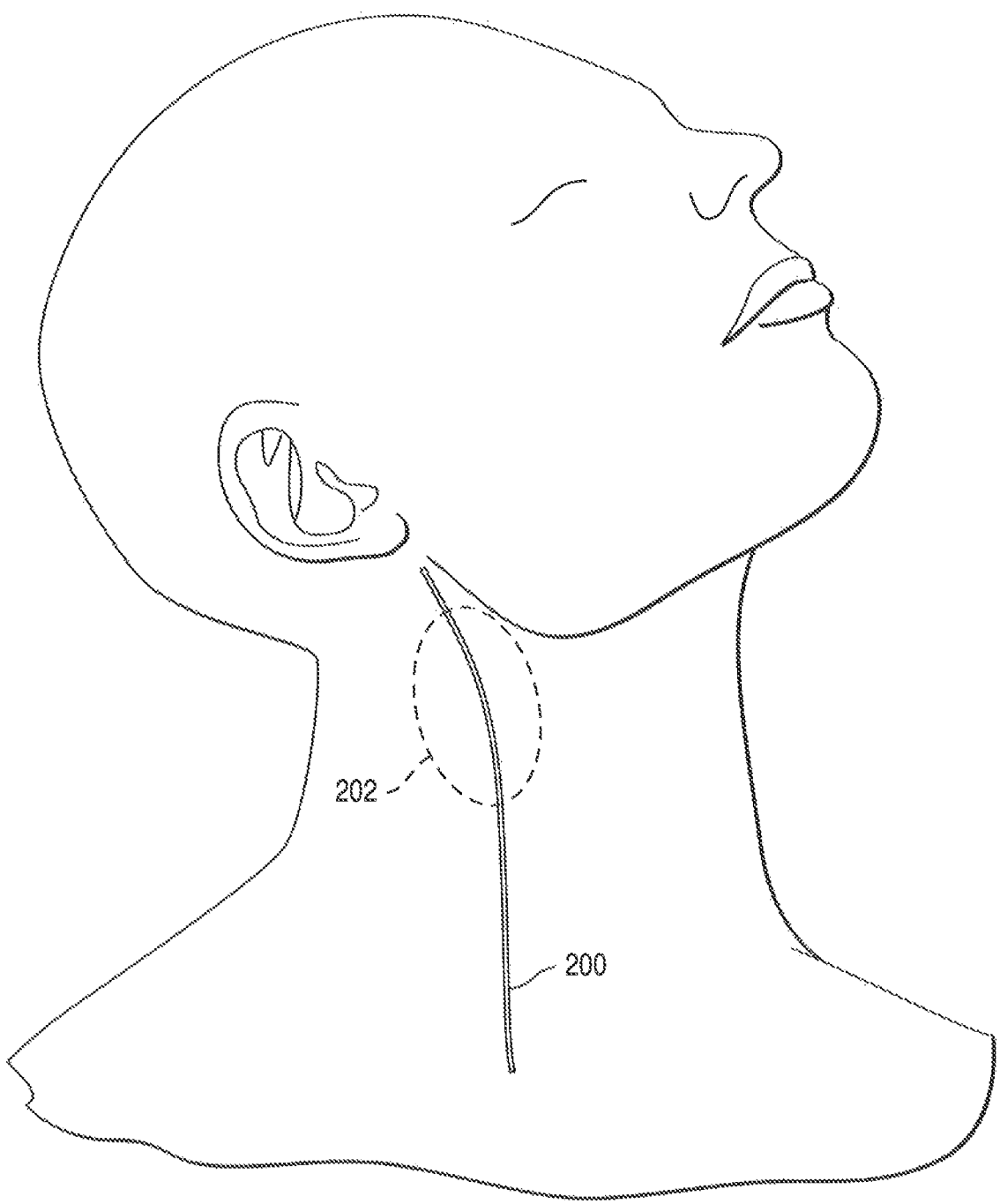
FIG. 16 is a side perspective view of a human head and neck showing the general location of the vagus nerve.

Vagal nerve stimulation may cause acute relief of primary headaches, migraines, asthma, exercise-induced bronchospasms and COPD. Additionally, it may be used for prophylactic treatments against migraine and cluster headaches. Only slight modifications of phrenic nerve stimulation paradigm described above are necessary to stimulate the vagus nerve. To stimulate the vagus nerve 200, the electrode ensemble is positioned on a skin region 202 on the neck and beneath the mandible (FIG. 16). Specifically, the cathode 20 is placed between the sternocleidomastoid muscle and trachea. A marker of autonomic activity (i.e., heart rate; cutaneous blood flow changes) is used to indicate vagal nerve activation.

Hypoglossal Nerve Stimulation Procedure

Obstructive sleep apnea is treated by stimulating the hypoglossal nerve, or branches thereof. Only slight modifications to the phrenic nerve stimulation paradigm as described herein is necessary. Additionally, a sensor may be used to coordinate stimulation with the respiratory patterns. The electrode ensemble will deliver stimulation to the hypoglossal nerve (or branches thereof) from a site on the upper neck or chin, and sense respiratory movements generated by the diaphragm muscle or autonomic nervous system. The stimulation is designed to remove the soft tissues (i.e., tongue) from impeding the airway.

EXPERIMENTS

Fifteen healthy volunteers ranging in age from 21 to 40 years underwent electrophysiological testing to determine if surface electrical stimulation could drive diaphragm muscle contractions in humans without causing pain, unwanted muscle contractions, and in a physiological fashion.

In accordance with the method described herein, the cathode of the present disclosure was placed at the posterior border of the sternocleidomastoid muscle and lightly pressed against the skin. A corresponding anode was applied to the posterior surface of the neck at midline.

Constant-current pulses were delivered in a single pulse and multi-pulse (1 second pulse train) fashion to each subject. Pulse durations ranged from 50-150 µs at intensities of less than 10 mA, and with various frequencies (10, 15, 20, and 25 Hz) and ramp-rates. The ramped pulse trains were delivered for a 1 second period and pulse durations of 100 µs. As described above, the intensity of each pulse is slightly increased (0 to 0.4 mA) from that of the preceding pulse. The intensity of the first few pulses was too weak to elicit diaphragm muscle contractions (sub-motor threshold).

Figure 9:
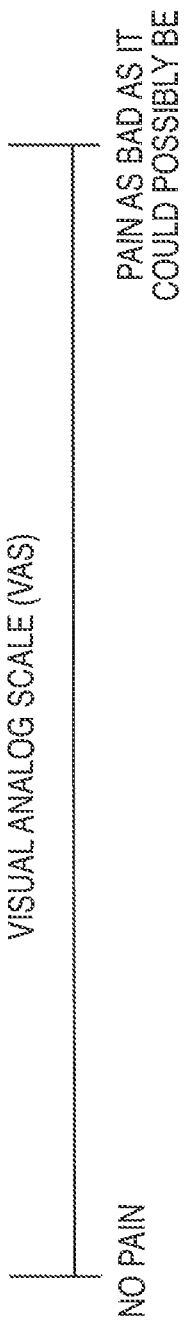
FIG. 9 is a chart showing the visual analog scale (VAS)

Outcome measures included: 1) electromyogram signals recorded from the diaphragm muscle; 2) electrocardiograms to determine heart-rate variability; 3) respiration, and 4) Visual-Analog-Scale (VAS). The VAS (FIG. 9) is a generally accepted method of determining the level of perceived pain.

Figure 4:
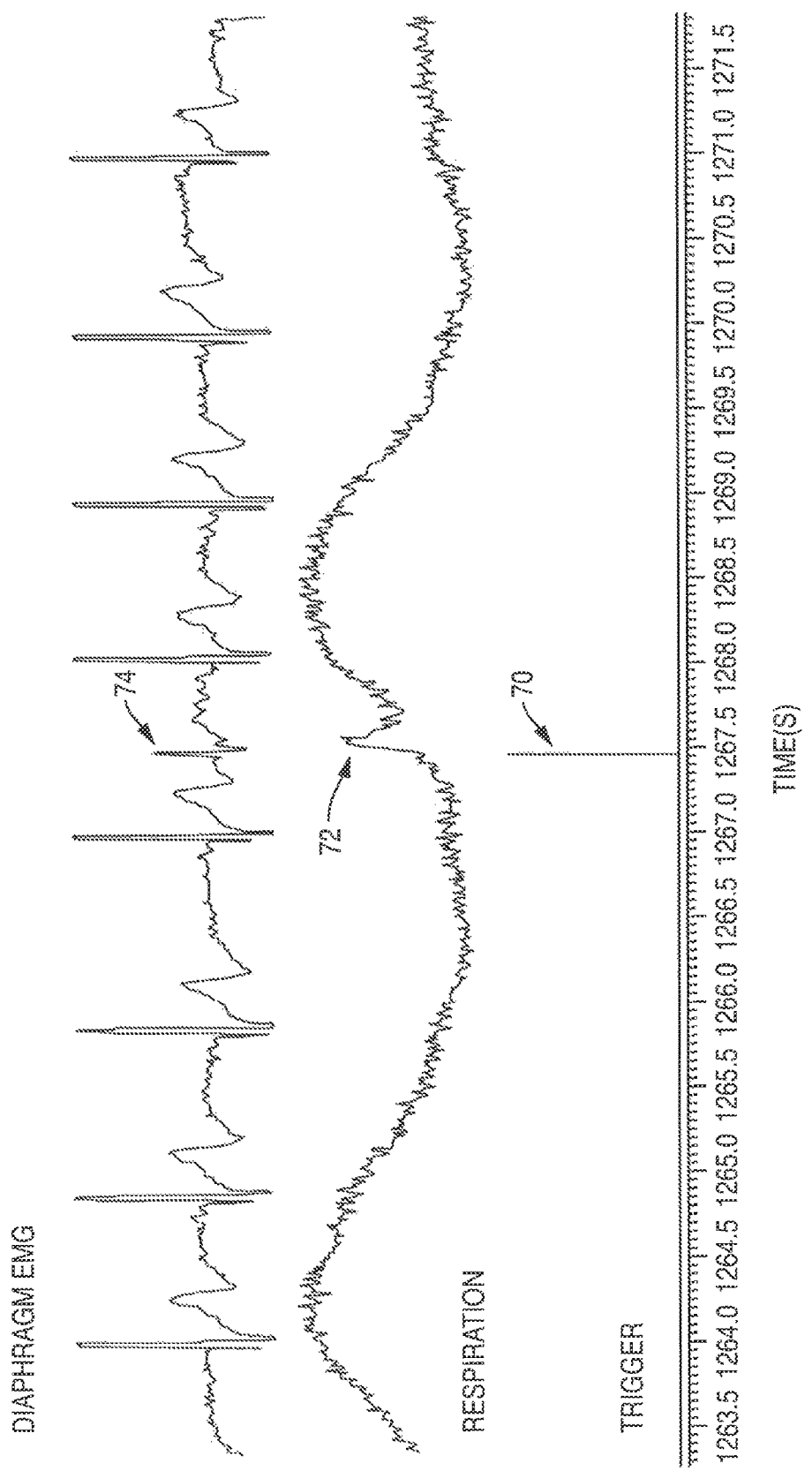
FIG. 4 is a graphical representation showing EMG and respiratory response to a single pulse (duration: 100 µs) of electrical stimulation in an able-bodied subject.

The results showed the single pulse 70 of electrical stimulation to the phrenic nerve activated the diaphragm muscle in humans (FIG. 4), without causing pain or unwanted muscle contractions. The single pulse 70 corresponds to an abrupt increase in respiration (see respiration spike 72), and an abrupt change in the diaphragm (see ECG spike 74). Importantly, all subjects indicated a VAS score of "zero" and similarly reported that stimulation felt like a spontaneously produced hiccup. Stimulation did not elicit changes in heart-rate.

Figure 5:
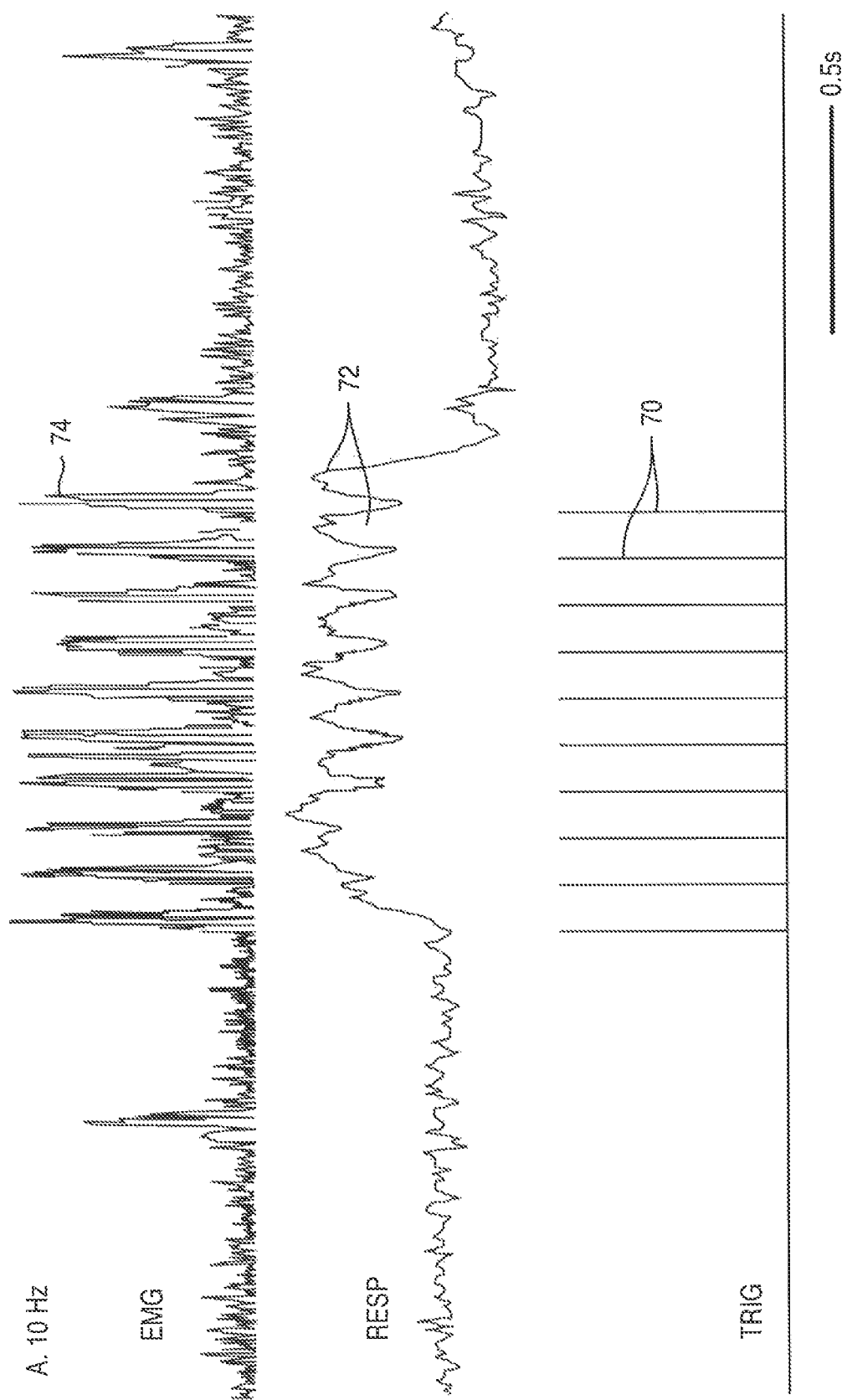
FIG. 5 is a graphical representation of the respiration response due to an electrical stimulation according to a method of the present disclosure, at a frequency of 10 Hz.
Figure 6:
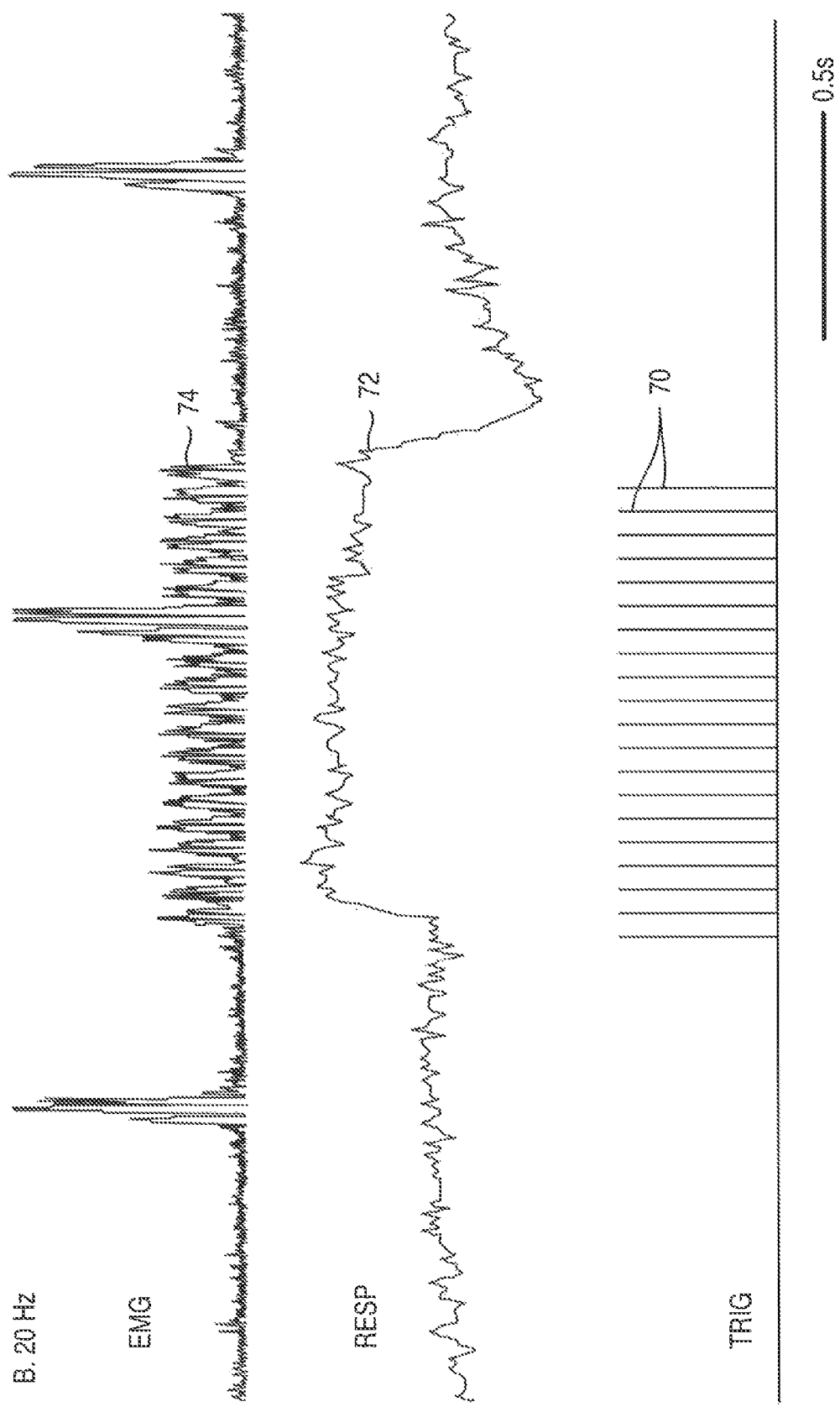
FIG. 6 is a graphical representation of the respiration response due to an electrical stimulation according to a method of the present disclosure, at a frequency of 20 Hz.

Multi-pulse electrical stimulation at frequencies greater than 20 Hz enabled a fused diaphragm muscle contraction. See FIG. 6 showing multiple pulses 70 which correspond to a fused respiratory spike 72, and multiple but compacted diaphragm spikes 74. This is in contrast to the non-fused response seen at 10 Hz. See FIG. 5 showing multiple pulses 70 which correspond to multiple respiratory spikes 72 and multiple diaphragm spikes 74.

Figure 7:
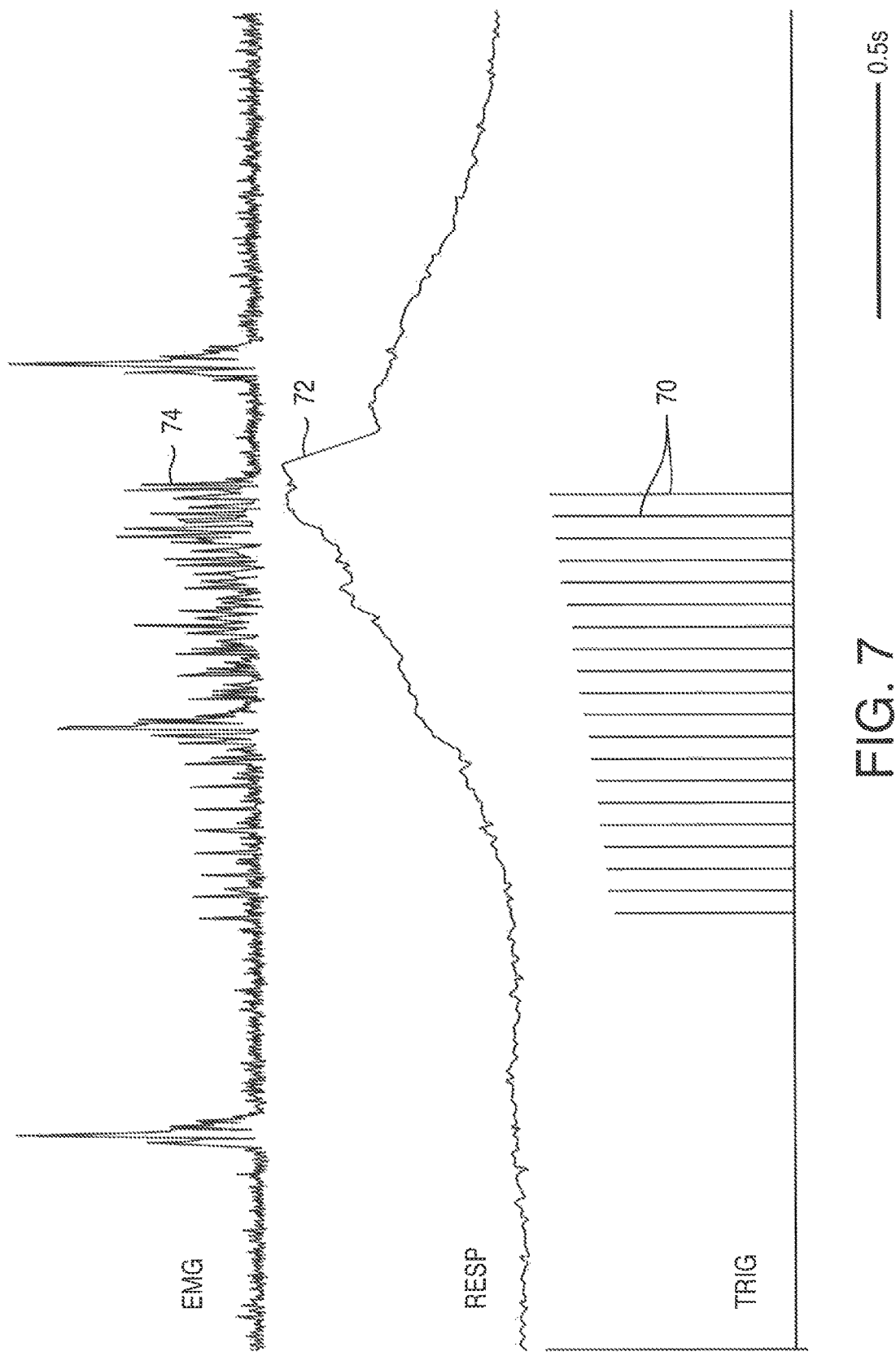
FIG. 7 is a graphical representation of the respiration response due to an electrical stimulation according to a method of the present disclosure, at the frequency of FIG. 5, and with a ramped current pulse train.

Ramped multi-pulse stimulation results in gradually increasing diaphragm muscle contraction and a smooth inhalation. See FIG. 7 showing multiple pulses 70 (at 20 Hz) wherein the current increases over time. The fused spike 74 also has a ramped shape. The multiple diaphragm spikes 74 are also increased over time. Again, the subjects reported a pain level of zero on the VAS indicating that the method of the present disclosure elicited a physiological diaphragm muscle contraction without recruiting pain receptors.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A system for delivering an electrical nerve stimulation through the intact skin of a mammal to stimulate an underlying target nerve to cause a muscle contraction, the system comprising:
   an electrode ensemble comprising a cathode and an anode, wherein the cathode defines a generally uniform skin contacting surface, the skin contacting surface of the cathode has an area of from about 1.5 mm$^2$ to about 40 mm$^2$; wherein a skin contacting surface of the anode has an area that is the same as or larger than the area of the skin contacting surface of the cathode; and wherein an inter-electrode distance between the cathode and the anode is adjustable; and
   an electronic control system electrically attached to the electrode ensemble, wherein the electronic control system delivers electrical stimulation through the electrode ensemble to stimulate the target nerve underlying the cathode to cause the muscle contraction without eliciting a pain sensation.

2. The system of claim 1, further comprising a component for monitoring a physiological function of the mammal, wherein delivery of the electrical nerve stimulation is coordinated with the physiological function.

3. The system of claim 2, wherein the physiological function is a respiratory cycle.

4. The system of claim 1, wherein the electrical nerve stimulation has a constant current of about 0.1 mA to about 20 mA.

5. The system of claim 1, wherein the electrical nerve stimulation is applied at a frequency ranging from about 1 Hz to about 45 Hz.

6. The system of claim 5, wherein the electrical nerve stimulation further includes a carrier frequency ranging from about 1 kilohertz to about 1 megahertz.

7. The system of claim 5, wherein the electrical nerve stimulation is a current having a square-wave pulse, and a pulse train that varies in amplitude and frequency.

8. The system of claim 7, wherein the square-wave pulse has a pulse-duration of less than about 250 µs.

9. The system of claim 7, wherein the pulse train is ramped.

10. The system of any one of claim 1, wherein the target nerve is a phrenic nerve, a vagal nerve, or a hypoglossal nerve.

11. The system of claim 10, wherein the target nerve is the phrenic nerve, wherein electrical nerve stimulation of the phrenic nerve strengthens a diaphragm muscle of the mammal to facilitate weaning of the mammal off a ventilator.

12. The system of claim 1, wherein the generally uniform skin contacting surface of the cathode is generally hemispherical, hemispheroidal, or ellipsoidal.

13. The system of claim 1, wherein the skin contacting surface of the cathode has an area of from about 3.5 mm$^2$ to about 20 mm$^2$.

14. The system of claim 1, the cathode includes a head and a shaft, wherein a hood of a shroud device partially covers the head and a neck of the shroud device partially covers the shaft.

15. The system of claim 14, wherein the hood is configured to rotate around the head to facilitate direction of the electrical nerve stimulation to the target nerve.

16. The system of claim 1, wherein the cathode and anode are attached to a collar or wrap in a spaced-apart configuration.

17. A method for delivering an electrical nerve stimulation through the intact skin of a mammal to elicit nerve signal transmission in an underlying target nerve to cause a muscle contraction, the method comprising:
- locating a target nerve;
- positioning a cathode on the skin over the target nerve, wherein the cathode defines a generally uniform skin contacting surface having an area of from about 3.5 mm$^2$ to about 40 mm$^2$;
- positioning a corresponding anode on the skin adjacent the cathode, wherein an inter-electrode distance between the cathode and the anode is adjustable; and
- delivering electrical nerve stimulation through the cathode to elicit nerve signal transmission in a target nerve underlying the cathode to cause the muscle contraction without eliciting pain sensations.

18. The method of claim 17, further comprising monitoring a physiological function of the mammal, wherein delivering the electrical nerve stimulation comprises coordinating the electrical nerve stimulation with the physiological function.

19. The method of claim 17, wherein the electrical nerve stimulation has a constant current of about 0.1 mA to about 20 mA and the electrical nerve stimulation frequency ranges from about 1 Hz to 45 Hz.

20. A kit for an electrical nerve stimulation procedure, the kit comprising:
- one or more cathodes, each cathode defining a generally uniform skin contacting surface, the skin contacting surface of each cathode having an area of from about 3.5 mm$^2$ to about 40 mm$^2$;
- one or more anodes, each anode having a skin contacting surface, the skin contacting surface of each anode having an area that is the same as or larger than the area of the skin contacting surface of each cathode; and wherein, in use, an inter-electrode distance between the one or more cathodes and the one or more anodes is adjustable; and
- electrical leads for connecting the one or more cathodes and the one or more anodes to an electronic control system for delivering electrical stimulation through the one or more cathodes to stimulate a target nerve underlying the one or more cathodes to cause a muscle contraction without eliciting a pain sensation.

* * * * *